US00PP32547P2

(12) United States Plant Patent
Schroll

(10) Patent No.: US PP32,547 P2
(45) Date of Patent: Dec. 1, 2020

(54) ***HYDRANGEA* PLANT NAMED 'SCHROLL43-13-01'**

(50) Latin Name: *Hydrangea macrophylla*
Varietal Denomination: SCHROLL43-13-01

(71) Applicant: Soren Schroll, Odense (DK)

(72) Inventor: Soren Schroll, Odense (DK)

(73) Assignee: SCHROLL MANAGEMENT ApS, Odense (DK)

( * ) Notice: Subject to any disclaimer, the term of this patent is extended or adjusted under 35 U.S.C. 154(b) by 0 days.

(21) Appl. No.: 16/873,039

(22) Filed: Jan. 21, 2020

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. A. Whealy

(57) ABSTRACT

A new and distinct cultivar of *Hydrangea* plant named 'SCHROLL43-13-01', characterized by its upright and mounded plant habit; moderately vigorous growth habit; freely branching habit and strong stems; dark green-colored leaves; large mophead-type inflorescences with white-colored sterile flowers; long flowering period; good postproduction quality and longevity and relatively good garden performance.

2 Drawing Sheets

Figure 1:
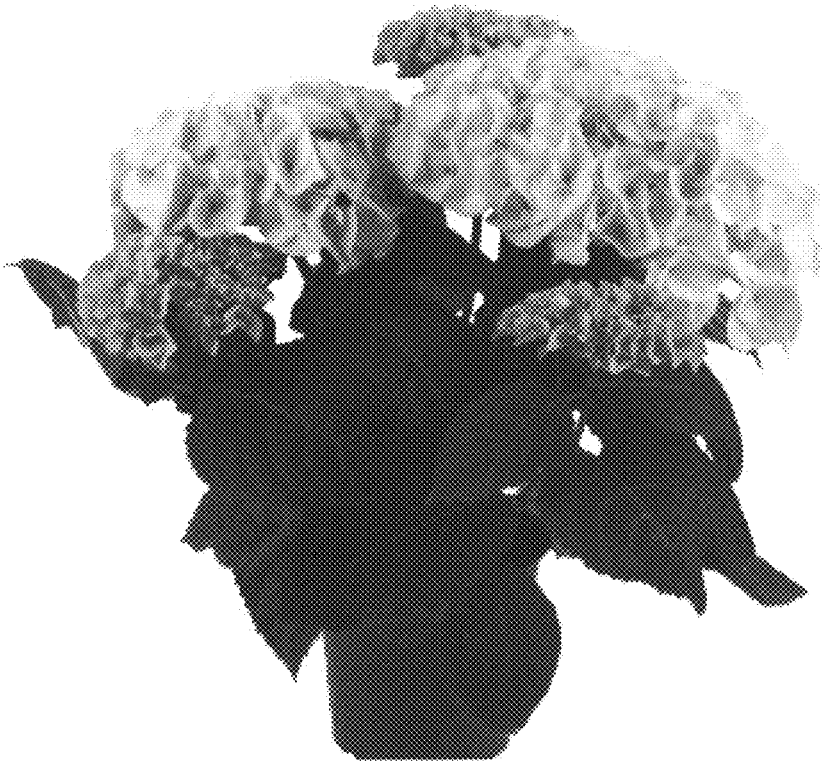

Botanical designation: *Hydrangea macrophylla.*
Cultivar denomination: 'SCHROLL43-13-01'.

BACKGROUND OF THE INVENTION

The present invention relates to a new and distinct cultivar of *Hydrangea* plant, botanically known as *Hydrangea macrophylla* and hereinafter referred to by the name 'SCHROLL43-13-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2013 of a proprietary selection of *Hydrangea macrophylla* identified as code number 144-09, not patented, as the female, or seed, parent with a proprietary selection of *Hydrangea macrophylla* identified as code number 100-00, not patented, as the male, or pollen, parent. The new *Hydrangea* plant was discovered and selected by the Inventor in February, 2015 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2015 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL43-13-01'. These characteristics in combination distinguish 'SCHROLL43-13-01' as a new and distinct *Hydrangea* plant:

1. Upright and mounded plant habit.
2. Moderately vigorous growth habit.
3. Freely branching habit and strong stems.
4. Dark green-colored leaves.
5. Large mophead-type inflorescences with white-colored sterile flowers.
6. Long flowering period.
7. Good postproduction quality and longevity and relatively good garden performance.

Plants of the new *Hydrangea* differ primarily from plants of the female selection parent in the following characteristics:

1. Plants of the new *Hydrangea* have stronger and denser inflorescences than plants of the female parent selection.
2. Plants of the new *Hydrangea* tolerate forcing treatments better than plants of the female parent selection.
3. Plants of the new *Hydrangea* initiate flowers more readily than plants of the female parent selection.

Plants of the new *Hydrangea* differ primarily from plants of the male selection parent in the following characteristics:

1. Plants of the new *Hydrangea* are more compact than and not as vigorous as plants of the male parent selection.
2. Stems of plants of the new *Hydrangea* are green in color whereas stems of plants of the male parent selection are dark greyed purple in color.

3. Inflorescences of plants of the new *Hydrangea* are more rounded and denser than inflorescences of plants of the male parent selection.
4. Plants of the new *Hydrangea* and the male parent selection differ in sterile flower color as sterile flowers of plants of the new *Hydrangea* are white in color whereas sterile flowers of plants of the male parent selection are pink in color.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are more compact than and not as vigorous as plants of 'H213901'.
2. Plants of the new *Hydrangea* have larger leaves than plants of 'H213901'.
3. Inflorescences of plants of the new *Hydrangea* are larger, denser and more rounded than inflorescences of plants of 'H213901'.
4. Sepals of sterile flowers of the new *Hydrangea* are not as undulate as sepals of sterile flowers of 'H213901'.
5. Plants of the new *Hydrangea* and 'H213901' differ in sterile flower color as sterile flowers of plants of the new *Hydrangea* are white in color whereas sterile flowers of plants of 'H213901' are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are more vigorous than plants of 'H213906'.
2. Plants of the new *Hydrangea* force faster than plants of 'H213906'.
3. Plants of the new *Hydrangea* and 'H213906' differ in sterile flower color as sterile flowers of plants of the new *Hydrangea* are white in color whereas sterile flowers of plants of 'H213906' are dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) comprises a side perspective view of a typical flowering plant of 'SCHROLL43-13-01' grown in a container.

Figure 2:
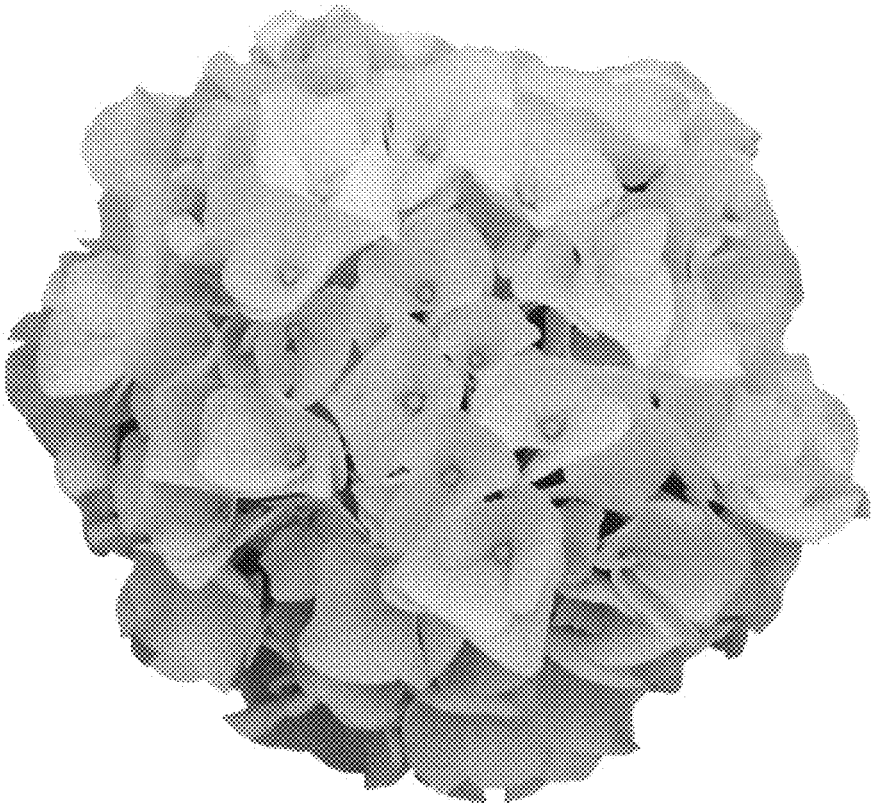

The photograph on the second sheet (FIG. 2 of 2) is a close-up view of a typical inflorescence of 'SCHROLL43-13-01'.

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. Plants are typically not "blued", that is, treated with aluminum sulfate to change the color of the inflorescences. In the following description, color references are made to The Royal Horticultural Society Colour Chart, 2007 Edition, except where general terms of ordinary dictionary significance are used.

Botanical description: *Hydrangea macrophylla* 'SCHROLL43-13-01'.

Parentage:

*Female, or seed, parent*.—Proprietary selection of *Hydrangea macrophylla* identified as code number 144-09, not patented.

*Male, or pollen, parent*.—Proprietary selection of *Hydrangea macrophylla* identified as code number 100-00, not patented.

Propagation:

*Type cutting*.—By softwood cuttings.

*Time to initiate roots, summer*.—About two weeks at temperatures about 20° C.

*Time to initiate roots, winter*.—About 17 to 18 days at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Sparse; not freely branching.

Plant description:

*Plant and growth habit*.—Perennial subshrub; upright and mounded plant habit; broadly inverted triangle; freely branching habit with about four to six lateral branches developing per plant; strong lateral branches; moderately vigorous growth habit.

*Plant height*.—About 30 cm.

*Plant diameter or area of spread*.—About 35 cm.

*Lateral branches*.—Length: About 13 cm to 18 cm. Diameter: About 4 mm to 6 mm. Internode length: About 4 cm to 6 cm. Strength: Strong, sturdy. Texture: Smooth, glabrous. Color, developing and developed: Close to 144A to 144B. Color, lenticels: Close to 79A.

Leaf description:

*Arrangement*.—Opposite, decussate; simple.

*Length*.—About 11 cm to 13 cm.

*Width*.—About 7 cm to 9 cm.

*Shape*.—Ovate.

*Apex*.—Apiculate to cuspidate.

*Base*.—Decurrent.

*Margin*.—Serrate.

*Texture, upper surface*.—Smooth to rugose, glabrous.

*Texture, lower surface*.—Rugose, glabrous.

*Venation pattern*.—Pinnate, reticulate.

*Color*.—Developing leaves, upper surface: Close to 137A. Developing leaves, lower surface: Close to 137D. Fully expanded leaves, upper surface: Close to 139A; venation, close to 145C to 145D. Fully expanded leaves, lower surface: Close to 137D; venation, close to 145C to 145D.

*Petioles*.—Length: About 1 cm to 3 cm. Diameter: About 3 mm to 5 mm. Strength: Strong. Texture, upper and lower surfaces: Smooth, glabrous. Color, upper and lower surfaces: Close to 143A.

Inflorescence & flower description:

*Flower type and habit*.—Showy single sterile and inconspicuous single fertile flowers arranged on terminal mophead-type panicles; panicles rounded globular in overall shape; fertile flowers (if present) face upright to outwardly and sterile flowers face mostly upright to outwardly depending on their position on the inflorescence; early flowering habit, plants begin flowering about eight to ten weeks after forcing period.

*Natural flowering season*.—Long flowering period, continuous flowering from the late summer (August) until frost in Northern Europe.

*Flower longevity, fertile flowers*.—Flowers last less than one month weeks on the plant; fertile flowers not persistent.

*Flower longevity, sterile flowers*.—Flowers last about four months on the plant; sterile flowers persistent.

*Quantity of flowers*.—Freely flowering habit with about 50 fertile flowers and about 150 sterile flowers per panicle.

*Fragrance*.—None detected.

*Panicle height*.—About 8 cm to 10 cm.

*Panicle diameter*.—About 18 cm to 20 cm.

*Flower diameter, fertile flowers*.—About 1 mm to 2 mm.

*Flower depth* (*height*), *fertile flowers*.—About 1 mm to 2 mm.

*Flower diameter, sterile flowers*.—About 6 cm.

*Flower depth* (*height*), *sterile flowers*.—About 1.5 cm.

*Flower shape, fertile flowers*.—Spherical.

*Flower shape, sterile flowers*.—Rounded, flat to upwardly bending.

*Flower buds, fertile flowers*.—Length: About 3 mm. Diameter: About 3 mm. Shape: Spherical. Color: Close to 155C.

*Flower buds, sterile flowers*.—Length: About 3 mm. Diameter: About 3 mm. Shape: Spherical. Color: Close to 155C.

*Petals, fertile flowers*.—Quantity and arrangement: If present, about four to five. Length: About 4 mm. Width: About 2 mm. Shape: Ovate. Apex: Rounded. Base: Cuneate. Margin: Entire. Texture, upper and lower surfaces: Smooth, glabrous. Color: When opening, upper and lower surfaces: Close to 145A. Fully opened, upper surface: Close to 155A; color does not change with development. Fully opened, lower surface: Close to 155B; color does not change with development.

*Petals, sterile flowers*.—Quantity and arrangement: If present about four in a single whorl. Length: About 2.3 mm. Width: About 1.2 mm. Shape: Ovate. Apex: Acute. Base: Rounded to truncate. Margin: Entire. Texture, upper and lower surfaces: Smooth, glabrous. Color: When opening, upper and lower surfaces: Close to NN155B. Fully opened, upper and lower surfaces: Close to 155D; color does not change with development.

*Sepals, fertile flowers*.—Quantity and arrangement: About five in a single whorl. Length: About 2 mm to 3 mm. Width: About 1 mm to 2 mm. Shape: Deltoid. Apex: Acute. Base: Cuneate. Margin: Entire. Texture, upper surface: Smooth, glabrous. Texture, lower surface: Pilose. Color: When opening, upper and lower surfaces: Close to 144C. Fully opened, upper and lower surfaces: Close to 143D; towards the apex, close to 63B to 63C; color becoming closer to 139D with development.

*Sepals, sterile flowers*.—Quantity and arrangement: Four in a single whorl. Length: About 3 cm. Width: About 3.5 cm. Shape: Deltoid to ovate. Apex: Obtuse. Base: Broadly cuneate. Margin: Entire. Texture, upper surface: Smooth to slightly rippled, glabrous. Texture, lower surface: Smooth, glabrous. Color: When opening, upper and lower surfaces: Initially, close to 150C; subsequently becoming closer to 155D. Fully opened, upper surface: Close to 155D; color becoming closer to 145C with development. Fully opened, lower surface: Close to NN155B; color becoming closer to 145C with development.

*Pedicels, fertile flowers*.—Length: About 7 mm to 9 mm. Diameter: About 1 mm. Strength: Strong. Aspect: Upright to outwardly. Texture: Pilose. Color: Close to 149D.

*Pedicels, sterile flowers*.—Length: About 3 cm. Diameter: About 2 mm. Strength: Strong. Aspect: Less than 90° from vertical. Texture: Slightly pubescent. Color: Close to 145A.

*Reproductive organs, fertile flowers*.—Stamens: Quantity per flower: About eight. Filament length: About 2 mm. Filament color: Close to 150B. Anther length: About 1 mm. Anther shape: Oblong. Anther color: Close to 155D. Pollen amount: Sparse. Pollen color: Close to 155D. Pistils: Pistil quantity per flower: About three. Pistil length: About 1 mm to 2 mm. Stigma shape: Oblong. Stigma color: Close to 150D. Style length: About 1 mm. Style color: Close to 149C. Ovary color: Close to 149C.

*Reproductive organs, sterile flowers*.—Stamens: Quantity per flower: About eight to ten. Filament length: About 3 mm to 4 mm. Filament color: Close to 155D. Anther length: About 1 mm. Anther shape: Ovate. Anther color: Close to 155D. Pollen amount: Scarce. Pollen color: Close to 155D. Pistils: To date, pistil development has not been observed on plants of the new *Hydrangea*.

*Seeds* (*on fertile flowers only*).—Quantity per fertile flower: About 20 to 50. Length: Less than 1 mm. Diameter: Less than 1 mm. Color: Greyish brown.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to 38° C.

It is claimed:

1. A new and distinct *Hydrangea* plant named 'SCHROLL43-13-01' as illustrated and described.

* * * * *